United States Patent [19]
Pfrengle

[11] Patent Number: 5,994,360
[45] Date of Patent: Nov. 30, 1999

[54] FUNGICIDAL 5-ALKYL-TRIAZOLOPYRIMIDINES

[75] Inventor: Waldemar Pfrengle, Seibersbach, Germany

[73] Assignee: American Cyanamid Company, Madison, N.J.

[21] Appl. No.: 09/115,496

[22] Filed: Jul. 14, 1998

Related U.S. Application Data

[60] Provisional application No. 60/052,407, Jul. 14, 1997.

[51] Int. Cl.$^6$ .......................... C07D 487/04; A01N 43/54
[52] U.S. Cl. .......................... 514/258; 544/263; 544/118; 514/233.2
[58] Field of Search ............................ 544/263; 514/258

[56] References Cited

U.S. PATENT DOCUMENTS

| | | | |
|---|---|---|---|
| 4,567,263 | 1/1986 | Eicken et al. | 544/263 |
| 5,593,996 | 1/1997 | Pees et al. | 514/258 |
| 5,817,663 | 10/1998 | Pees et al. | 544/263 |

FOREIGN PATENT DOCUMENTS 5500113  12/1992   European Pat. Off. ...... C07D 487/04

*Primary Examiner*—Mukund J. Shah
*Assistant Examiner*—Ann Kessinger
*Attorney, Agent, or Firm*—Timothy J. Babcock

[57] ABSTRACT

The novel compounds of formula I:

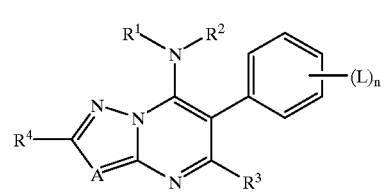

(I)

(A, L, n and $R^1$ through $R^4$ are defined in the specification) show selective fungicidal activity. The new compounds can be combined with carriers and adjuvants to form fungicidal compositions.

14 Claims, No Drawings

FUNGICIDAL 5-ALKYL-TRIAZOLOPYRIMIDINES

This application claims priority from copending provisional application(s) Ser. No, 60/052407 filed on Jul. 14, 1997.

BACKGROUND OF THE INVENTION

This invention relates to certain triazolopyrimidine compounds, a process for their preparation, compositions containing such compounds, a method for combating a fungus at a locus comprising treating the locus with such compounds and their use as fungicides.

U.S. Pat. No. 4,567,263 claims compounds of the general formula

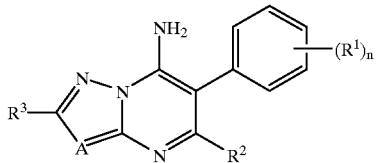

in which $R^1$ represents alkyl, halogen, alkoxy, cyano, cycloalkyl, aryl, aryloxy, arylthio, aralkyl, arylalkyl, arylalkyloxy or arylalkylthio each optionally substituted by halogen or alkoxy; or $(R^1)_n$ represents a benzene, indane or tetrahydronaphthalene ring fused with the phenyl ring, aromatic moieties in the above groups being optionally substituted by alkyl, alkoxy, halogen or cyano; n is 1 or 2; $R^2$ and $R^3$ are each hydrogen, alkyl or aryl, A represents a nitrogen atom or a $CR^4$ group, and $R^4$ is as $R^2$ but can also be halogen, cyano or alkoxycarbonyl or together with $R^3$ can form an alkylene chain containing up to two double bonds. The compounds are said to be active against various phytopathogenic fungi, especially those of the phycomycete class. However evidence of fungicidal activity is only provided for these compounds against *Plasmopara viticola*, a member of the oomycete class of fungi.

U.S. Pat. No. 5,593,996 claims compounds of the general formula

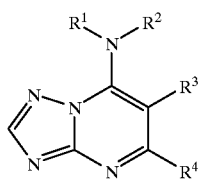

in which $R^1$ represents an optionally substituted alkyl, alkenyl, alkadienyl, cycloalkyl, bicycloalkyl or heterocyclyl group; $R^2$ represents a hydrogen atom or an alkyl group; or $R^1$ and $R^2$ together with the interjacent nitrogen atom represent an optionally substituted heterocyclic ring; $R^3$ represents an optionally substituted phenyl or naphthyl group; and $R^4$ represents a halogen atom or a group $-NR^5R^6$ where $R^5$ represents a hydrogen atom or an amino, alkyl, cycloalkyl or bicycloalkyl group and $R^6$ represents a hydrogen atom or an alkyl group.

SUMMARY OF THE INVENTION

The present invention provides a compound of formula I

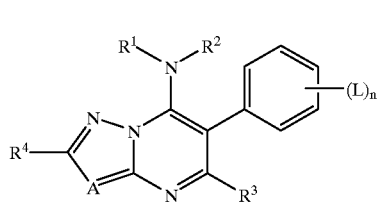

in which $R^1$ represents an optionally substituted alkyl, alkenyl, alkynyl, alkadienyl, aryl, heteroaryl, cycloalkyl, bicycloalkyl or heterocyclyl group, $R^2$ represents a hydrogen atom or an optionally substituted alkyl, alkenyl, alkynyl, alkadienyl, aryl, heteroaryl, cycloalkyl, bicycloalkyl or heterocyclyl group, or $R^1$ and $R^2$ together with the interjacent nitrogen atom represent an optionally substituted heterocyclic ring, $R^3$ represents an alkyl group, $R^4$ represents hydrogen or an alkyl or aryl group, L represents halogen or an optionally substituted alkyl or alkoxy group, A represents N or $CR^5$, wherein $R^5$ has the meaning given for $R^4$, and n is 0 or an integer from 1 to 5.

The new compounds show an excellent selective fungicidal activity in various crops.

It is an object of the present invention to provide novel, selective fungicidal compounds.

It is also an object of the invention to provide methods for controlling undesired fungus by contacting said plants with a fungicidally effective amount of the new compounds.

It is another object of the invention to provide selective fungicidal compositions containing the new compounds as active ingredients.

These and other objects and features of the invention will be more apparent from the detailed description set forth hereinbelow, and from the appended claims.

DETAILED DESCRIPTION OF THE PREFERRED EMBODIMENTS

It has surprisingly been found that the compounds of formula I

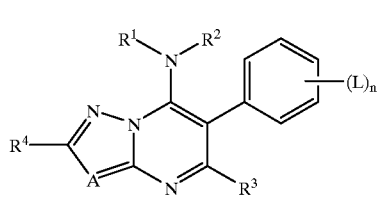

in which $R^1$ through $R^4$, A, L and n have the meaning given above for formula I show an excellent fungicidal activity against a broad range of fungi.

In general terms, unless otherwise stated, as used herein the term halogen atom may denote a bromine, iodine, chlorine or fluorine atom, and is especially a bromine, chlorine or fluorine atom.

Optionally substituted moieties may be unsubstituted or have from one up to the maximal possible number of substituents. Typically, 0 to 2 substituents are present.

In general terms, unless otherwise stated herein, the terms alkyl, alkenyl, alkynyl, alkadienyl as used herein with respect to a radical or moiety refer to a straight or branched chain radical or moiety. As a rule, such radicals have up to 10, in particular up to 6 carbon atoms. Suitably an alkyl moiety has from 1 to 6 carbon atoms, preferably from 1 to 3 carbon atoms. A preferred alkyl moiety is an ethyl or especially a methyl group. Suitably an alkenyl moiety has from 2 to 6 carbon atoms. A preferred alkenyl moiety is allyl or especially a 2-methylallyl group.

Unless otherwise stated herein, the term aryl, as used herein with respect to a radical or moiety, refers to an aryl group having 6, 10 or 14 carbon atoms, preferably 6 or 10 carbon atoms, in particular phenyl being optionally substituted by one or more halogen atoms, nitro, cyano, alkyl, preferably $C_{1-6}$ alkyl, alkoxy, preferably $C_{1-6}$ alkoxy.

Generally, unless otherwise stated herein, the term heteroaryl, as used herein with respect to a radical or moiety, refers to a heteroaryl group having 5 or 6 ring atoms selected from carbon, nitrogen, oxygen and sulfur, at least one of which being nitrogen, oxygen or sulfur.

Unless otherwise stated herein, the term cycloalkyl, as used herein with respect to a radical or moiety, refers to a cycloalkyl group having 3 to 8 carbon atoms, preferably 5 to 7 carbon atoms, in particular cyclohexyl being optionally substituted by one or more halogen atoms, nitro, cyano, alkyl, preferably $C_{1-6}$ alkyl, alkoxy, preferably $C_{1-6}$ alkoxy.

Furthermore, unless otherwise stated herein, the term heterocyclyl or heterocyclic ring, as used herein with respect to a radical or moiety, refers to a saturated heterocyclyl group having 5 or 6 ring atoms selected from carbon, nitrogen, oxygen and sulfur, at least one of which being nitrogen, oxygen or sulfur being optionally substituted by one or more halogen atoms, nitro, cyano, alkyl, preferably $C_{1-6}$ alkyl, alkoxy, preferably $C_{1-6}$ alkoxy, in particular pyrrolidinyl, pyrazolidinyl, piperidinyl, piperazinyl or morpholin-4-yl.

The invention especially relates to compounds of the general formula I in which any alkyl part of the groups $R^1$ through $R^4$ which may be straight chained or branched, contains up to 10 carbon atoms, preferably up to 9 carbon atoms, more preferably up to 6 carbon atoms, any alkenyl or alkynyl part of the substituents $R^1$ through $R^4$ contains up to 10 carbon atoms, preferably up to 9 carbon atoms, more preferably up to 6 carbon atoms, any cycloalkyl part of the substituents $R^1$ through $R^4$ contains from 3 to 10 carbon atoms, preferably from 3 to 8 carbon atoms, more preferably from 3 to 6 carbon atoms, and any aryl part of the substituents $R^1$ through $R^4$ contains 6, 10 or 14 carbon atoms, preferably 6 or 10 carbon atoms, and in which each optionally substituted group independently is substituted by one or more halogen atoms or nitro, cyano, alkyl, preferably $C_{1-6}$ alkyl, cycloalkyl, preferably $C_{3-6}$ cycloalkyl, cycloalkenyl, preferably $C_{3-6}$ cycloalkenyl, haloalkyl, preferably $C_{1-6}$ haloalkyl, halocycloalkyl, preferably $C_{3-6}$ halocycloalkyl, alkoxy, preferably $C_{1-6}$ alkoxy, haloalkoxy, preferably $C_{1-6}$ haloalkoxy, phenyl, halo- or dihalo-phenyl or pyridyl groups. Any alkyl, alkenyl or alkynyl group may be linear or branched. A 4- to 6- membered heterocyclic group may be any heterocyclic group with 4 to 6 ring atoms, interrupted by one or more heteroatoms selected from sulfur, nitrogen, and oxygen, preferably oxygen. A halogen atom suitably denotes a fluorine, chlorine or bromine atom.

The invention especially relates to compounds of the general formula I in which $R^1$ represents a $C_{1-10}$ alkyl, $C_{1-10}$ haloalkyl, $C_{3-6}$ cycloalkyl, $C_{3-8}$ cycloalkyl-$C_{1-6}$ alkyl, $C_{1-10}$ alkoxy-$C_{1-6}$ alkyl or phenyl group, in particular a fluorinated $C_{1-10}$ alkyl group and $R^2$ represents a $C_{1-10}$ alkyl, $C_{3-6}$ cycloalkyl, $C_{3-8}$ cycloalkyl-$C_{1-6}$ alkyl, $C_{1-10}$ alkoxy-$C_{1-6}$ alkyl or phenyl group, in particular a hydrogen atom.

Particularly preferred are compounds of formula I, in which the phenyl group

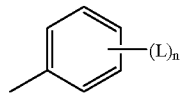

is selected from

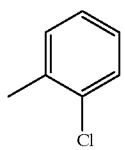

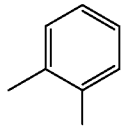

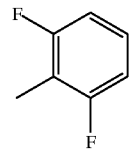

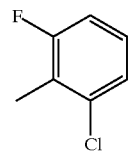

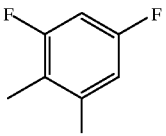

and

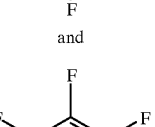

The compounds according to general formula I are oils, gums, or, predominantly crystalline solid materials. They are superior through their valuable fungicidal properties, in particular their enhanced systemicity and enhanced fungitoxicity against tomato early blight. For example, they can be used in agriculture or related fields for the control of phytopathogenic fungi such as *Alternaria solani, Botrytis cinerea, Cercospora beticola, Cladosporium herbarum, Corticium rolfsii, Erysiphe graminis, Helminthosporium tritici repentis, Leptosphaeria nodorum, Micronectriella* nivalis, Monilinia fructigena, Mycosphaerella ligulicola, Mycosphaerella pinodes, Pyricularia grisea f.sp. oryzae, Rhizoctonia solani and Sclerotinia sclerotiorum, in particular for the control of Alternaria solani and Botrytis cinerea. The compounds of general formula I according to the invention possess a high fungicidal activity within a wide concentration range and may be used in agriculture without any difficulties.

Moreover, the compounds according to the invention show enhanced residual control of fungi compared with conventional fungicides.

Good results in terms of control of phythopathogenic fungi are obtained with a compound as defined in formula I wherein:

$R^3$ represents a methyl group;

$R^1$ represents straight chained or branched $C_1$–$C_6$-alkyl, in particular ethyl or isopropyl, $C_{3-7}$-cycloalkyl, in particular cyclopentyl, straight chained or branched $C_1$–$C_6$-haloalkyl, in particular 2,2,2-trifluoroethyl or 1,1,1-trifluoroprop-2-yl, or straight chained or branched $C_2$–$C_6$-alkenyl, in particular allyl or 2-methylallyl, and $R^2$ represents hydrogen or $C_1$–$C_6$-alkyl, in particular nydrogen methyl or ethyl; or $R^1$ and $R^2$ together with the interjacent nitrogen atom represent a heterocyclic ring with 5 or 6 carbon atoms being optionally substituted with one or two $C_1$–$C_6$-alkyl groups, in particular in which $R^1$ and $R^2$ together with the interjacent nitrogen atom represent an optionally substituted pyridin-1-yl group, such as piperidin-1-yl or 4-methylpiperidin-1-yl;

A is N, and $R^4$ is hydrogen;

In particularly preferred are the compounds of formula IA,

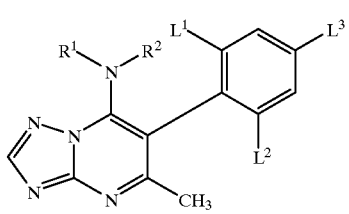

(IA)

in which $R^1$ and $R^2$ have the meaning given, and $L^1$, $L^2$ and $L^3$ each independently represent hydrogen, fluorine or chlorine at least one of which being fluorine or chlorine.

Especially good results in terms of control of phytopathogenic fungi are obtained by using, for example, the following compounds of formula I: 6-(2-chloro-6-fluorophenyl)-5-methyl-7-(4-methylpiperidin-1-yl)-[1,2,4]triazolo[1,5-a]pyrimidine; 6-(2-fluorophenyl)-5-methyl-7-(4-methylpiperidin-1-yl)-[1,2,4]triazolo[1,5-a]pyrimidine; 6-(2-chlorophenyl)-5-methyl-7-(4-methylpiperidin-1-yl)-[1,2,4]triazolo[1,5-a]pyrimidine; 6-(2-chloro-6-fluorophenyl)-5-methyl-7-(N,N-diethylamino)-[1,2,4]triazolo[1,5-a]pyrimidine; 6-(2-chloro-6-fluorophenyl)-5-methyl-7-(N-ethylamino)-[1,2,4]triazolo[1,5-a]pyrimidine; 6-(2-chloro-6-fluorophenyl)-5-methyl-7-(N-(2,2,2-trifluoroethyl)-amino)-[1,2,4]triazolo[1,5-a]pyrimidine; 6-(2,6-difluorophenyl)-5-methyl-7-(4-methylpiperidin-1-yl)-[1,2,4]triazolo[1,5-a]pyrimidine; 6-(2,6-dichlorophenyl)-5-methyl-7-(4-methylpiperidin-1-yl)-[1,2,4]triazolo[1,5-a]pyrimidine; 6-(2-chloro-6-fluorophenyl)-5-methyl-7-(N-isopropylamino)-[1,2,4]triazolo[1,5-a]pyrimidine; 6-(2-chloro-6-fluorophenyl)-5-methyl-7-(N-cyclopentylamino)-[1,2,4]triazolo[1,5-a]pyrimidine; 6-(2,6-difluorophenyl)-5-methyl-7-(N,N-diethylamino)-[1,2,4]triazolo[1,5-a]pyrimidine and 6-(2-chloro-6-fluorophenyl)-5-methyl-7-(N-ethyl-N-2-methylallyl-amino)-[1,2,4]triazolo[1,5-a]pyrimidine, 6-(2,4,6-trifluorophenyl)-5-methyl-7-(4-methylpiperidin-1-yl)-[1,2,4]triazolo[1,5-a]pyrimidine; (2,4,6-trifluorophenyl)-5-methyl-7-(piperidin-1-yl)-[1,2,4]triazolo[1,5-a]pyrimidine; (2-chloro-6-fluorophenyl)-5-methyl-7-(piperidin-1-yl)-[1,2,4]triazolo[1,5-a]pyrimidine; (2-fluorophenyl)-5-methyl-7-(piperidin-1-yl)-[1,2,4]triazolo[1,5-a]pyrimidine; 6-(2-chloro-6-fluorophenyl)-5-methyl-7-(N-(1,1,1-trifluoroprop-2-yl)-amino)-[1,2,4]triazolo[1,5-a]pyrimidine; 6-(2,6-difluorophenyl)-5-methyl-7-(N-(1,1,1-trifluoroprop-2-yl)-amino)-[1,2,4]triazolo[1,5-a]pyrimidine; 6-(2,4,6-trifluorophenyl)-5-methyl-7-(N-(1,1,1-trifluoroprop-2-yl)-amino)-[1,2,4]triazolo[1,5-a]pyrimidine; 6-(2,4,6-trifluorophenyl)-5-methyl-7-(N,N-diethylamino)-[1,2,4]triazolo[1,5-a]pyrimidine; 6-(2,4,6-trifluorophenyl)-5-methyl-7-(N-ethylamino)-[1,2,4]triazolo[1,5-a]pyrimidine.

The present invention further provides a process for the preparation of a compound of formula I, wherein $R^3$ represents a methyl group, which comprises (a) treating a 5-halo-azolopyrimidine of formula II,

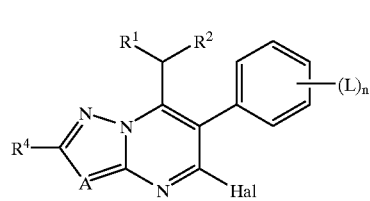

(II)

in which A, $R^1$, $R^2$ $R^4$, L and n have the meaning given for formula I, with an alkyl malonate in the presence of a base, (b) heating the resulting aminoazolopyrimidin-5-ylmalonate of formula III,

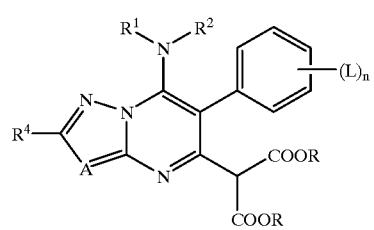

(III)

in which $R^1$, $R^2$, $R^4$, A, L and n have the meaning given in the preceding claims, and R represents an alkyl group in the presence of an acid.

Furthermore, the compounds of formula I may also be prepared from the 7-aminotriazolopyrimidines of formula IV,

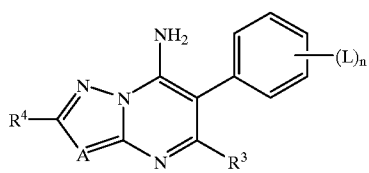

in which $R^3$, $R^4$, A, L and n have the meaning given in the preceding claims, which are treated with a halogenating agent in the presence of a diazotising agent, and treating the resulting compound of the general formula V

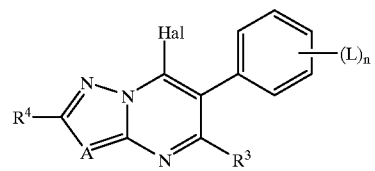

in which
$R^3$, $R^4$, A, L and n are as defined above; and
Hal represents a chlorine or bromine atom,
with an amine of the general formula VI

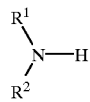

in which
$R^1$ and $R^2$ are as defined above.

Compounds of formula IV are known e.g. from U.S. Pat. No. 4,567,263.

The reaction between the 5- halo-7-amino-6-phenyl-triazolopyrimidines of formula II, which are known from U.S. Pat. No. 5,593,996, and the alkyl malonate is conveniently carried out in the presence of a solvent. Suitable solvents include ethers, such as dioxane, diethyl ether and, especially, tetrahydrofuran, optionally halogenated hydrocarbons such as mineral oil, dichloromethane and aromatic hydrocarbons, for example toluene, nitrites such as acetonitrile or mixtures of these solvents. The reaction is suitably carried out at a temperature in the range from 0° C. to 100° C., the preferred reaction temperature being from 20° C. to 70° C. It is also preferred that the reaction is carried out in the presence of a strong base. Suitable strong bases include hydrides such as sodium hydride and organometallic compounds such as butyllithium and amides such as sodium amide or lithium diisopropylamide.

The compounds of general formula I have been found to have fungicidal activity. Accordingly the invention further provides a fungicidal composition which comprises a carrier and, as active ingredient, at least one compound of formula I as defined above. A method of making such a composition is also provided which comprises bringing a compound of formula I as defined above into association with at least one carrier. Such a composition may contain a single compound or a mixture of several compounds of the present invention. It is also envisaged that different isomers or mixtures of isomers may have different levels or spectra of activity and thus compositions may comprise individual isomers or mixtures of isomers.

A composition according to the invention preferably contains from 0.5% to 95% by weight of active ingredient.

A carrier in a composition according to the invention is any material with which the active ingredient is formulated to facilitate application to the locus to be treated, which may for example be a plant, seed or soil, or to facilitate storage, transport or handling. A carrier may be a solid or a liquid, including material which is normally gaseous but which has been compressed to form a liquid, and any of the carriers normally used in formulating fungicidal compositions may be used.

The compositions may be manufactured into e.g. emulsion concentrates, solutions which may be sprayed directly or diluted, diluted emulsions, wettable powders, soluble powders, dusts, granulates, water-dispersible granulates, microencapsulates by well-established procedures. The form of application such as spraying, atomizing, dispersing, pouring may be chosen like the compositions according to the desired objectives and the given circumstances.

The formulations, i.e. the compositions which comprise at least one compound according to general formula I and optionally solid and/or liquid auxiliaries and adjuvants, may be prepared by well-established procedures, e.g. intensive mixing and/or grinding of the active ingredients with other substances, such as fillers, solvents, solid carriers, and optionally surface-active compounds (tensides).

Solvents may be aromatic hydrocarbons, preferably the fractions $C_8$ to $C_{12}$, e.g. xylenes or xylene mixtures, substituted naphthalenes, phthalic acid esters, such as dibutyl or dioctyl phthalate, aliphatic hydrocarbons, e.g. cyclohexane or paraffins, alcohols and glycols as well as their ethers and esters, e.g. ethanol, ethyleneglycol mono- and dimethyl ether, ketones such as cyclohexanone, strongly polar solvents such as N-methyl 2-pyrrolidone, dimethyl sulfoxide, alkyl formamides, epoxidized vegetable oils, e.g. epoxidized coconut or soybean oil, water. Mixtures of different liquids are often suitable.

Solid carriers, which may be used for dusts or dispergible powders, may be mineral fillers, such as calcite, talc, kaolin, montmorillonite, attapulgite. The physical properties may be improved by addition of highly dispersed silica gel or highly dispersed polymers. Carriers for granulates may be porous material, e.g. pumice, broken brick, sepiolite, bentonite, non-sorptive carriers may be calcite or sand. Additionally, a multitude of pre-granulated inorganic or organic materials may be used, such as dolomite or crushed plant residues.

Fungicidal compositions are often formulated and transported in concentrated form which is subsequently diluted by the user before application. The presence of small amounts of a carrier which is a surface-active agent facilitates this process of dilution. Thus, preferably one carrier in a composition according to the invention is a surface active agent. For example, the composition may contain at least two carriers, at least one of which is a surface active agent.

Suitable surface-active substances may be non-ionogenic, anionic or cationic tensides with good dispersing, emulgating and wetting properties depending on the nature of the compound according to general formula I to be formulated. Tensides may also mean mixtures of tensides.

Suitable tensides may be so-called water-soluble soaps as well as water-soluble synthetic surface-active compounds.

Soaps usually are alkali, earth alkali or optionally-substituted ammonium salts of higher fatty acids ($C_{10}$–$C_{20}$), e.g. the sodium or potassium salts of oleic or stearic acid or of mixtures of natural fatty acids which are prepared, for example, from coconut or tallow oil. Furthermore, methyl-taurine salts of fatty acids may be used.

However, so-called synthetic tensides are preferably used, especially fatty sulphonates, fatty sulfates, sulfonated benzimidazole derivatives or alkyl aryl sulphonates.

The fatty sulfates or fatty sulphonates are normally used as alkali, earth alkali or optionally-substituted ammonium salts and have an alkyl moiety of 8 to 22 carbon atoms, whereby alkyl also means the alkyl moiety of acyl residues, such as the sodium or calcium salt of lignin sulfonic acid, of sulfuric acid dodecylate or of a mixture of fatty alcohols prepared from natural fatty acids. This also includes the salts of sulfuric acid esters, sulfonic acids and adducts of fatty alcohols and ethylene oxide. The sulfonated benzimidazole derivatives preferably contain 2 sulfonic acid residues and a fatty acid residue with 8 to 22 carbon atoms. Alkyl aryl sulphonates are, for example, the sodium, calcium or triethyl ammonium salts of dodecyl benzene sulfonic acid, dibutyl naphthalene sulfonic acid or of a condensate of naphthalene sulfonic acid and formaldehyde.

Furthermore, phosphates, such as the salts of the phosphoric acid ester of a p-nonylphenol-(4-14)-ethylene oxide adduct or phospholipids, may be used.

Non-ionic tensides are preferably polyglycolether derivatives of aliphatic or cycloaliphatic alcohols, saturated or non-saturated fatty acids and alkylphenols, which have 3 to 10 glycol ether groups and 8 to 20 carbon atoms in the (aliphatic) hydrocarbon residue and 6 to 18 carbon atoms in the alkyl residue of the alkyl phenols.

Other suitable non-ionic tensides are the water-soluble, 20 to 250 ethylene glycol ether groups containing polyadducts of ethylene oxide and polypropylene glycol, ethylene diamino polypropylene glycol and alkyl polypropylene glycol with 1 to 10 carbon atoms in the alkyl moiety, the substances normally contain 1 to 5 ethylene glycol units per propylene glycol unit.

Examples of non-ionic tensides are nonylphenol polyethoxy ethanols, castor oil polyglycol ether, polyadducts of ethylene oxide and polypropylene, tributyl phenoxy polyethoxy ethanol, polyethylene glycol, octyl phenoxy polyethoxy ethanol.

Furthermore, fatty acid esters of polyoxy ethylene sorbitan, such as polyoxy ethylene sorbitan trioleate may be used.

Cationic tensides preferably are quaternary ammonium salts, which have at least one alkyl residue with 8 to 22 carbon atoms and, furthermore, low, optionally-halogenated alkyl, benzyl or hydroxyalkyl residues. The salts are preferably halides, methyl sulfates or alkyl sulfates, e.g. stearyl trimethyl ammonium chloride or benzyl bis(2-chloroethyl) ethyl ammonium bromide.

The compositions of the invention may for example be formulated as wettable powders, dusts, granules, solutions, emulsifiable concentrates emulsions, suspension concentrates and aerosols. Wettable powders usually contain 25%, 50% or 75% w/w of active ingredient and usually contain in addition to solid inert carrier, 3%–10% w/w of a dispersing agent and, where necessary, 0%–10% w/w of stabilizer(s) and/or other additives such as penetrants or stickers. Dusts are usually formulated as a dust concentrate having a similar composition to that of a wettable powder but without a dispersant, and may be diluted in the field with further solid carrier to give a composition usually containing 0.5%–10% w/w of active ingredient. Granules are usually prepared to have a size between 10 and 100 mesh ASTM (approx. 2.00 mm–0.15 mm), and may be manufactured by agglomeration or impregnation techniques. Generally, granules will contain 0.5%–75% active ingredient and 0–10% w/w of additives such as stabilizer, surfactants, slow release modifiers and binding agents. The so called "dry flowable powders" consist of relatively small granules having a relatively high concentration of active ingredient. Emulsifiable concentrates usually contain, in addition to a solvent or a mixture of solvents, 1%–50% w/v active ingredient, 2%–20% w/v emulsifiers and 0%–20% w/v of other additives such as stabilizers, penetrants and corrosion inhibitors. Suspension concentrates are usually compounded so as to obtain a stable, non-sedimenting flowable product and usually contain 10%–75% w/w active ingredient, 0.5%–15% w/w of dispersing agents, 0.1%–10% w/w of suspending agents such as protective colloids and thixotropic agents, 0%–10% of other additives such as defoamers, corrosion inhibitors, stabilizers, penetrants and stickers, and water or an organic liquid in which the active ingredient is substantially insoluble; certain organic solids or inorganic salts may be present dissolved in the formulation to assist in preventing sedimentation or as antifreeze agents for water.

Aqueous dispersions and emulsions, for example compositions obtained by diluting a wettable powder or a concentrate according to the invention with water, also lie within the scope of the invention. The said emulsions may be of the water-in-oil or of the oil-in-water type, and may have a thick 'mayonnaise' like consistency.

The composition of the invention may also contain other ingredients, for example other compounds possessing herbicidal, insecticidal or fungicidal properties.

Of particular interest in enhancing the duration of the protective activity of the compounds of this invention is the use of a carrier which will provide slow release of the fungicidal compounds into the environment of a plant which is to be protected. Such slow-release formulations could, for example, be inserted in the soil adjacent to the roots of a plant, or could include an adhesive component enabling them to be applied directly to the stem of a plant.

As commodity the compositions may preferably be in a concentrated form whereas the end-user generally employs diluted compositions. The compositions may be diluted to a concentration of 0.001% of active ingredient (a.i.). The doses usually are in the range from 0.01 to 10 kg a.i./ha.

The compositions of this invention can comprise also other compounds having biological activity, e.g. compounds having similar or complementary fungicidal activity or compounds having plant growth regulating, herbicidal or insecticidal activity.

These mixtures of fungicides can have a broader spectrum of activity than the compound of general formula I alone. Furthermore, the other fungicide can have a synergistic effect on the fungicidal activity of the compound of general formula I.

Examples of the other fungicidal compound are carbendazim, benomyl, thiophanate-methyl, thiabendazole, fuberidazole, etridiazole, dichlofluanid, cymoxanil, oxadixyl, ofurace, metalaxyl, furalaxyl, benalaxyl, fosetyl-aluminium, fenarimol, iprodione, procymidione, vinclozolin, penconazole, myclobutanil, R0151297, S3308, pyrazophos, ethirimol, ditalimfos, tridemorph, triforine, nuarimol, triazbutyl, guazatine, triacetate salt of 1,1'-iminodi (octamethylene)-diguanidine, propiconazole, prochloraz, flutriafol, hexaconazole, flusilazole, triadimefon, triadimenol, diclobutrazol, fenpropimorph, pyrifenox, cyproconazole, tebuconazole, epoxiconazole, 4-chloro-N-(cyano(ethoxy)methyl)benzamide, fenpropidin, chlorozolinate, diniconazol, imazalil, fenfuram, carboxin, oxycarboxin, methfuroxam, dodemorph, blasticidin S, kasugamycin, edifenphos, kitazin P, cycloheximide, phthalide, probenazole, isoprothiolane, tricyclazole, pyroquilon, chlorbenzthiazon, neoasozin, polyoxin D, validamycin A, mepronil, flutolanil, pencycuron, diclomezin, phenazineoxide, nickel dimethyldithiocarbamate, techlofthalam, bitertanol, bupirimate, etaconazole, streptomycin, cypofuram, biloxazol, quinomethionate, dimethirimol, 1-(2-cyano-2-methoxyimino-acetyl)-3-ethyl urea, fenapanil, tolclofosmethyl, pyroxyfur, polyram, maneb, mancozeb, captafol, chlorothalonil, anilazin, thiram, captan, folpet, zineb, propineb, sulfur, dinocap, binapacryl, nitrothalisopropyl, dodine, dithianon, fentin hydroxide, fentin acetate, tecnazene, quintozen, dichloran, copper-containing compounds such as copper oxychloride, copper sulfate and Bordeaux mixture as well as organic mercury compounds, kresoxim-methyl, azoxystrobin, SSF-126, pyrimethanil, cyprodinil, spiroxamine, fludioxonil, quinoxyfen, BION, carpropamid, metconazole, dimethomorph, famoxadone, propanocarb, flumetover, fenpiclonil, fluazinam, mepanipyrim, triazoxide, chlorothalonil.

The compounds of general formula I can be mixed with soil, peat or other rooting media for the protection of the plants against seed-borne, soil-borne or foliar fungal diseases.

The invention still further provides the use as a fungicide of a compound of the general formula I as defined above or a composition as defined above, and a method for combating fungus at a locus, which comprises treating the locus, which may be for example plants subject to or subjected to fungal attack, seeds of such plants or the medium in which such plants are growing or are to be grown, with such a compound or composition.

The present invention is of wide applicability in the protection of crop and ornamental plants against fungal attack. Typical crops which may be protected include vines, grain crops such as wheat and barley, rice, sugar beet, top fruit, peanuts, potatoes and tomatoes. The duration of the protection is normally dependent on the individual compound selected, and also a variety of external factors, such as climate, whose impact is normally mitigated by the use of a suitable formulation.

The following examples further illustrate the present invention. It should be understood, however, that the invention is not limited solely to the particular examples given below.

EXAMPLE 1

6-(2-Chloro-6-fluorophenyl)-5-methyl-7-(4-methylpiperidin-1-yl)-[1,2,4]triazolo[1.5a] pyrimidine 1A Diethyl [6-(2-chloro-6-fluorophenyl)-7-(4-methylpiperidin-1-yl)-[1,2,4-triazolo[1.5a] pyrimidine-5-yl]-malonate Sodium hydride (0.27 g of a 50% dispersion in mineral oil, 5.65 mmol) is added to diethylmalonate (20 ml). The mixture is diluted with acetonitrile and 6-(2-chloro-6-fluorophenyl)-5-chloro-7-(4 -methylpiperidin-1-yl)-[1,2,4] triazolo[1.5a]pyrimidine (obtained according to U.S. Pat. No. 5,593,996, 2.0 g, 4.71 mmol) is added. The reaction mixture is heated to 60° C. and stirred for 20 hours. Aqueous ammonium chloride (50 ml) is added and the mixture is acidified with diluted hydrochloric acid. The reaction mixture is extracted with ethyl acetate (3×50 ml). The combined organic phases are dried and concentrated. The residue is purified by column chromatography (silica, toluene:ethyl acetate, 9:1). The pure product is obtained as tan crystals (0.95 g) with a melting point of 162–163° C.

1B 6-(2-Chloro-6-fluorophenyl)-5-methyl-7-(4-methylpiperidin-1-yl)-[1,2,4]triazolo[1.5a] pyrimidine A mixture of 1A (0.5 g, 1 mmol) and concentrated hydrochloric acid is heated to 80° C. for 24 hours. The reaction mixture is cooled and adjusted to pH of 5 by addition of aqueous sodium hydroxide. The reaction mixture is extracted with ethyl acetate. The combined organic phases are dried and concentrated. The residue is purified by column chromatography (silica, toluene:ethyl acetate, 2:1). The pure product is obtained as tan crystals (0.27 g) with a melting point of 177–178° C.

EXAMPLES 2–12

The following examples (Table I; structure and melting point) are synthesized analogously to Example 1.

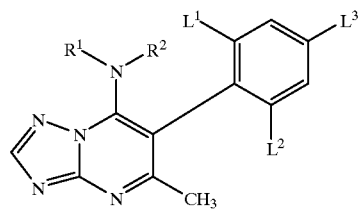

| Example | R¹ | R² | L¹ | L² | L³ | melting point (° C.) |
|---|---|---|---|---|---|---|
| 2 | —(CH₂)₂—CH(CH₃)—(CH₂)₂— | | F | H | H | 197–199 |
| 3 | —(CH₂)₂—CH(CH₃)—(CH₂)₂— | | Cl | H | H | 201–202 |
| 4 | C₂H₅— | C₂H₅— | F | Cl | H | 147–148 |
| 5 | C₂H₅— | H | F | Cl | H | 140–141 |
| 6 | F₃C—CH₂— | H | F | Cl | H | |
| 7 | —(CH₂)₂—CH(CH₃)—(CH₂)₂— | | F | F | H | |
| 8 | —(CH₂)₂—CH(CH₃)—(CH₂)₂— | | Cl | Cl | H | |
| 9 | 2-propyl | H | F | Cl | H | |
| 10 | cyclopentyl | H | F | Cl | H | |
| 11 | C₂H₅— | C₂H₅— | F | F | H | |
| 12 | CH₂=C(CH₃)—CH₂— | C₂H₅— | F | Cl | H | |
| 13 | —(CH₂)₂—CH(CH₃)—(CH₂)₂— | | F | F | F | |
| 14 | —(CH₂)₅— | | F | F | F | |
| 15 | —(CH₂)₅— | | F | Cl | H | |
| 16 | —(CH₂)₅— | | F | H | H | |
| 17 | —(CH₂)₅— | | F | F | H | |
| 18 | 1,1,1-trifluoroprop-2-yl | H | F | Cl | H | |
| 19 | 1,1,1-trifluoroprop-2-yl | H | F | F | H | |
| 20 | 1,1,1-trifluoroprop-2-yl | H | F | F | F | |
| 21 | C₂H₅— | C₂H₅— | F | F | F | |
| 22 | C₂H₅— | H | F | F | F | |

Biological Investigations

Determination of Effective Dosis for 90% Inhibition by Test Compounds in the Serial Dilution Test with Various Phytopathogenic Fungi The ED>90 (Effective Dosis>90%)-value is determined by serial dilution tests using Microtiter plates with 24 or 48 wells per plate. The dilution of the test compounds in the nutrient solution and the distribution to the wells is carried out by a TECAN RSP 5000 Robotic Sample Processor. The following test compound concentrations are used: 0.05, 0.10, 0.20, 0.39, 0.78, 1.56, 3.13, 6.25, 12.50, 25.00, 50.00 and 100.00 mg/ml. For preparation of the nutrient solution, V8 vegetable juice (333 ml) is mixed with calcium carbonate (4.95 g), centrifuged, the supernatant (200 ml) diluted with water (800 ml) and autoclaved at 121° C. for 30 min.

The respective inocula (*Alternaria solani*, ALTESO; *Botrytis cinerea*, BOTRICI; *Leptosphaeria nodorum*, LEPTNO; *Phytophthora infestans*, PHYTIN; *Pyrenophora teres*, PYRNTE; *Rhizoctonia solani*, RHIZSO;) are added into the wells as spore suspensions (50 ml; 5×10⁵/ml) or agar slices (6 mm) of an agar culture of the fungus.

After 6–12 days incubation at suitable temperatures (1 8–25° C.), the ED>90 values are determined by visual inspection of the plates. The lowest concentration in the dilution series with mycelial growth of less than 10% is defined to be the ED>90 alue (Table II; n. t.=not tested).

TABLE II

| Ex. No. | ALTESO | BOTRCI | LEPTNO | PHYTIN | PYRNTE | RHISZO |
|---|---|---|---|---|---|---|
| 1 | 0.2 | 0.78 | 1.56 | n.t. | 0.78 | 50 |
| 2 | 3.13 | 12.5 | n.t. | 100 | 100 | n.t. |
| 3 | 0.78 | 1.56 | n.t. | n.t. | 100 | n.t. |
| 4 | 25 | n.t. | n.t. | n.t. | n.t. | 3.13 |
| 5 | 50 | 25 | n.t. | 100 | n.t. | 50 |

What is claimed is:

1. A compound of formula IA,

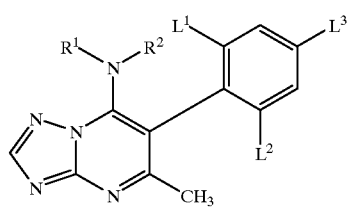

(IA)

in which
R¹ and R² together with the interjacent nitrogen atom represent a piperidin-1-yl or 4-methylpiperidin-1-yl ring, and
L¹, L² and L³ each independently represent hydrogen, fluorine or chlorine at least one of which being fluorine or chlorine.

2. A compound according to claim 1 selected from the group consisting of
6-(2-chloro-6-fluorophenyl)-5-methyl-7-(4-methylpiperidin-1-yl)-[1,2,4]triazolo[1,5-a]pyrimidine;
6-(2-fluorophenyl)-5-methyl-7-(4-methylpiperidin-1-yl)-[1,2,4]triazolo[1,5-a]pyrimidine;
6-(2-chlorophenyl)-5-methyl-7-(4-methylpiperidin-1-yl)-[1,2,4]triazolo[1,5-a]pyrimidine;
6-(2,6-difluorophenyl)-5-methyl-7-(4-methylpiperidin-1-yl)-[1,2,4]triazolo[1,5-a]pyrimidine;
6-(2,6-dichlorophenyl)-5-methyl-7-(4-methylpiperidin-1-yl)-[1,2,4]triazolo[1,5-a]pyrimidine;
6-(2,4,6-trifluorophenyl)-5-methyl-7-(4-methylpiperidin-1-yl)-[1,2,4]triazolo[1,5-a]pyrimidine;
6-(2,4,6-trifluorophenyl)-5-methyl-7-(piperidin-1-yl)-[1,2,4]triazolo[1,5-a]pyrimidine;
6-(2-chloro-6-fluorophenyl)-5-methyl-7-(piperidin-1-yl)-[1,2,4]triazolo[1,5-a]pyrimidine; and
6-(2-fluorophenyl)-5-methyl-7-(piperidin-1-yl)-[1,2,4]triazolo[1,5-a]pyrimidine.

3. A compound according to claim 1, wherein the compound is
6-(2-chloro-6-fluorophenyl)-5-methyl-7-(4-methylpiperidin-1-yl)-[1,2,4]triazolo[1,5a]pyrimidine.

4. A fungicidal composition which comprises a carrier, and as active agent, at least one compound of formula IA as defined in claim 1.

5. The composition according to claim 4 wherein the compound is selected from the group consisting of
6-(2-chloro-6-fluorophenyl)-5-methyl-7-(4-methylpiperidin-1-yl)-[1,2,4]triazolo[1,5-a]pyrimidine;
6-(2-fluorophenyl)-5-methyl-7-(4-methylpiperidin-1-yl)-[1,2,4]triazolo[1,5-a]pyrimidine;
6-(2-chlorophenyl)-5-methyl-7-(4-methylpiperidin-1-yl)-[1,2,4]triazolo[1,5-a]pyrimidine;
6-(2,6-difluorophenyl)-5-methyl-7-(4-methylpiperidin-1-yl)-[1,2,4]triazolo[1,5-a]pyrimidine;
6-(2,6-dichlorophenyl)-5-methyl-7-(4-methylpiperidin-1-yl)-[1,2,4]triazolo[1,5-a]pyrimidine;
6-(2,4,6-trifluorophenyl)-5-methyl-7-(4-methylpiperidin-1-yl)-[1,2,4]triazolo[1,5-a]pyrimidine;
6-(2,4,6-trifluorophenyl)-5-methyl-7-(piperidin-1-yl)-[1,2,4]triazolo[1,5-a]pyrimidine;
6-(2-chloro-6-fluorophenyl)-5-methyl-7-(piperidin-1-yl)-[1,2,4]triazolo[1,5-a]pyrimidine; and
6-(2-fluorophenyl)-5-methyl-7-(piperidin-1-yl)-[1,2,4]triazolo[1,5-a]pyrimidine.

6. The composition according to claim 4 wherein the compound is
6-(2-chloro-6-fluorophenyl)-5-methyl-7-(4-methylpiperidin-1-yl)-[1,2,4]triazolo[1,5-a]pyrimidine.

7. A method of combating fungus at a locus which comprises treating the locus with a fungicidally effective amount of a compound of formula IA as defined in claim 1.

8. The method according to claim 7 wherein the fungus is selected from the group consisting of *Bortrytis cinera*, *Alternaria solani* and *Pyrenophora teres*.

9. The method according to claim 7 wherein the compound is selected from the group consisting of
6-(2-chloro-6-fluorophenyl)-5-methyl-7-(4-methylpiperidin-1-yl)-[1,2,4]triazolo[1,5-a]pyrimidine;
6-(2-fluorophenyl)-5-methyl-7-(4-methylpiperidin-1-yl)-[1,2,4]triazolo[1,5-a]pyrimidine;
6-(2-chlorophenyl)-5-methyl-7-(4-methylpiperidin-1-yl)-[1,2,4]triazolo[1,5-a]pyrimidine;
6-(2,6-difluorophenyl)-5-methyl-7-(4-methylpiperidin-1-yl)-[1,2,4]triazolo[1,5-a]pyrimidine;
6-(2,6-dichlorophenyl)-5-methyl-7-(4-methylpiperidin-1-yl)-[1,2,4]triazolo[1,5-a]pyrimidine;
6-(2,4,6-trifluorophenyl)-5-methyl-7-(4-methylpiperidin-1-yl)-[1,2,4]triazolo[1,5-a]pyrimidine;

6-(2,4,6-trifluorophenyl)-5-methyl-7-(piperidin-1-yl)-[1,2,4]triazolo[1,5-a]pyrimidine;

6-(2-chloro-6-fluorophenyl)-5-methyl-7-(piperidin-1-yl)-[1,2,4]triazolo[1,5-a]pyrimidine; and 6-(2-fluorophenyl)-5-methyl-7-(piperidin-1-yl)-[1,2,4]triazolo[1,5-a]pyrimidine.

10. The method according to claim 11 wherein the compound is 6-(2-chloro-6-fluorophenyl)-5-methyl-7-(4-methylpiperidin-1-yl)-[1,2,4]triazolo[1,5-a]pyrimidine.

11. A process for the preparation of a compound of formula I

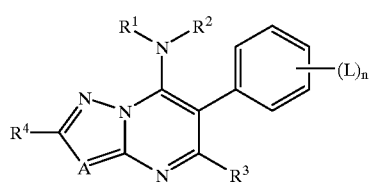
(I)

in which

R$^1$ represents an optionally substituted alkyl, alkenyl, alkynyl, alkadienyl, aryl or cycloalkyl group, R$^2$ represents a hydrogen atom or an optionally substituted alkyl, alkenyl, alkynyl, alkadienyl, aryl or cycloalkyl group, or R$^1$ and R$^2$ together with the interjacent nitrogen atom represent a saturated heterocyclic ring with 5 or 6 carbon atoms being optionally substituted with one or two C$_{1-6}$ alkyl groups, R$^3$ represents methyl, R$^4$ represents hydrogen, L represents halogen or an alkyl or alkoxy group, A represents N, and n is 0 or an integer from 1 to 5, and in which each optionally substituted group is independently substituted by one or more halogen atoms or nitro, cyano, C$_{1-6}$ alkyl, C$_{3-6}$ cycloalkyl, C$_{3-6}$ cycloalkenyl, C$_{1-6}$ haloalkyl, C$_{3-6}$ halocycloalkyl, C$_{1-6}$ alkoxy, C$_{1-6}$ haloalkoxy, phenyl, halo- or dihalo-phenyl or pyridyl groups, which comprises (a) treating a 5-halo-azolopyrimidine of formula II,

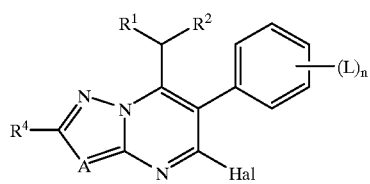
(II)

in which A, R$^1$, R$^2$, L and n have the meaning given for formula I, and Hal represents a halogen atom with an alkyl malonate in the presence of a base, and (b) heating the resulting aminoazolopyrimidin-5-ylmalonate of formula III,

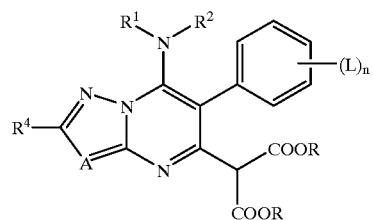
(III)

in which R$^1$, R$^2$, R$^4$, A, L and n have the meaning given for formula I, and R represents an alkyl group in the presence of an acid.

12. A compound of formula III

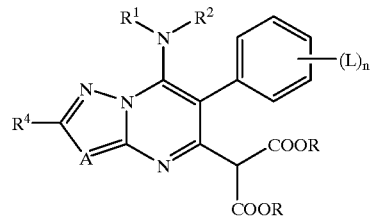
(III)

in which

R represents an alkyl group,

R$^1$ represents an optionally substituted alkyl, alkenyl, alkynyl, alkadienyl, aryl or cycloalkyl group, R$^2$ represents a hydrogen atom or an optionally substituted alkyl, alkenyl, alkynyl, alkadienyl, aryl or cycloalkyl group, or R$^1$ and R$^2$ together with the interjacent nitrogen atom represent a saturated heterocyclic ring with 5 or 6 carbon atoms being optionally substituted with one or two C$_{1-6}$ alkyl groups R$^4$ represents hydrogen, L represents halogen or an alkyl or alkoxy group, A represents N, and n is 0 or an integer from 1 to 5, and in which each optionally substituted group is independently substituted by one or more halogen atoms or nitro, cyano, C$_{1-6}$ alkyl, C$_{3-6}$ cycloalkyl, C$_{3-6}$ cycloalkenyl, C$_{1-6}$ haloalkyl, C$_{3-6}$ halocycloalkyl, C$_{1-6}$ alkoxy, C$_{1-6}$ haloalkoxy, phenyl, halo- or dihalo-phenyl or pyridyl groups.

13. The process according to claim 11 wherein R$^1$ and R$^2$ together with the interjacent nitrogen atom represent a piperidin-1-yl group optionally substituted with one or two C$_{1-6}$ alkyl groups.

14. The compound according to claim 12 wherein R$^1$ and R$^2$ together with the interjacent nitrogen atom represent a piperidin-1-yl group optionally substituted with one or two C$_{1-6}$ alkyl groups.

* * * * *